United States Patent [19]

Weetall et al.

[11] 4,024,235

[45] May 17, 1977

[54] DETECTION AND QUANTITATION OF VIRAL ANTIBODIES

[75] Inventors: Howard H. Weetall, Big Flats; Sidney Yaverbaum, Sufferin, both of N.Y.

[73] Assignee: Corning Glass Works, Corning, N.Y.

[22] Filed: July 21, 1975

[21] Appl. No.: 597,837

[52] U.S. Cl. .............................. 424/1; 23/253 TP; 424/8; 424/12; 424/86; 424/89; 424/93

[51] Int. Cl.² ................ A61K 39/12; A61K 43/00; G01N 31/22; G01N 33/16

[58] Field of Search ............... 424/8, 12, 86, 89, 1, 424/85, 93; 23/230, 253 TP

[56] References Cited

UNITED STATES PATENTS 3,652,761 3/1972 Weetall ........................ 424/85 X

*Primary Examiner*—Albert T. Meyers
*Assistant Examiner*—A. P. Fagelson
*Attorney, Agent, or Firm*—James A. Giblin; Clinton S. Janes, Jr.; Clarence R. Patty, Jr.

[57] ABSTRACT

Method of detecting and/or quantitating anti-virus antibodies comprising the steps of reacting serum containing an unknown amount of a given antibody, a known amount of the antibody (radioactively labelled), and a composite consisting of the antibodies coupled chemically through an intermediate silane coupling agent to a porous glass body, the composite having complexed thereto quantities of the virus; separating the composite from the reaction solution after a suitable reaction period; determining the radioactivity count of the separated composite or the remaining solution; and, relating the count to a standard curve.

8 Claims, 1 Drawing Figure

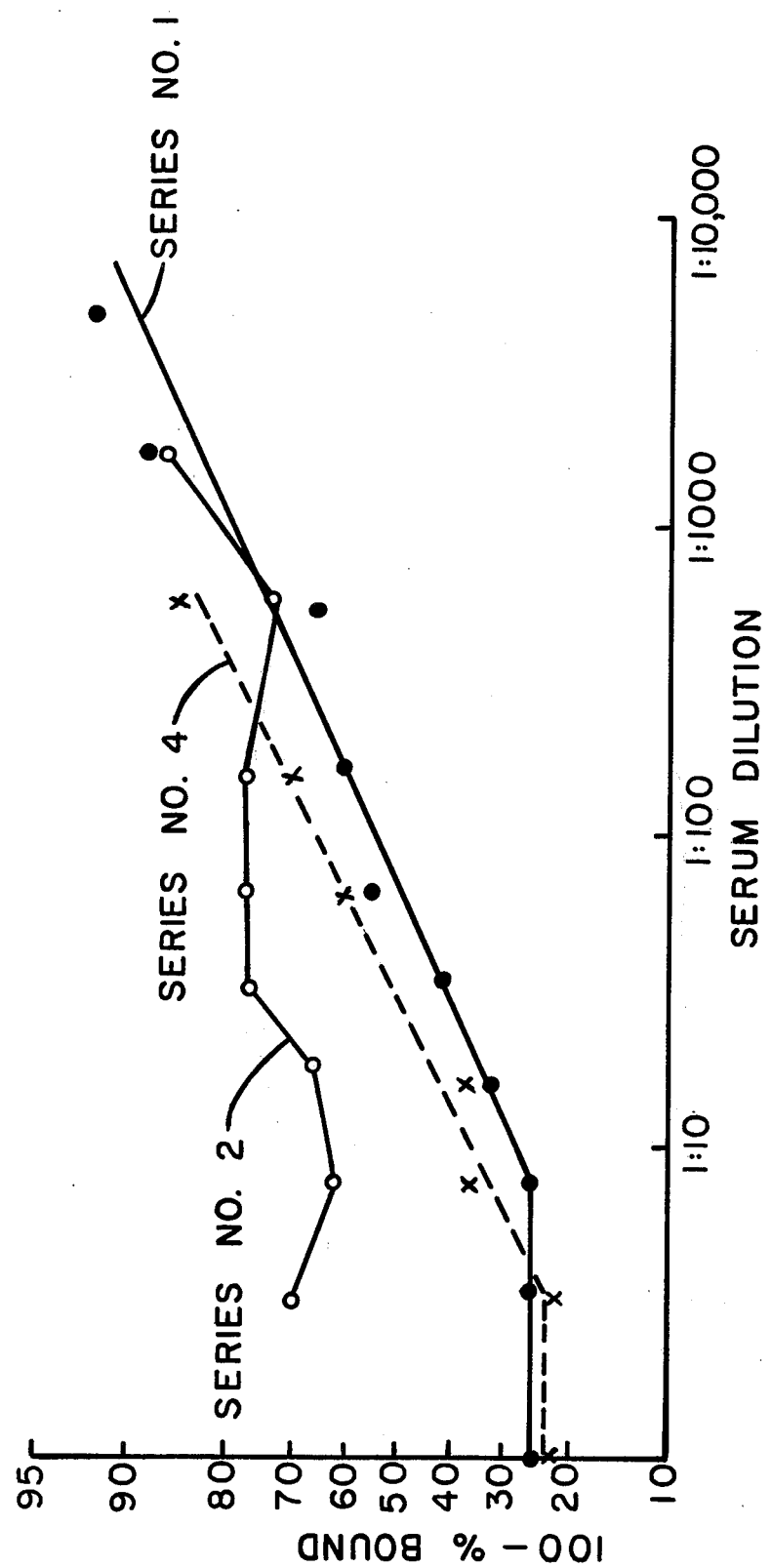

DETECTION AND QUANTITATION OF VIRAL ANTIBODIES

BACKGROUND OF THE INVENTION

1. Field

This invention relates generally to radioassays and specifically to a solid phase radioimmunoassay for the detection and/or quantitation of viral antibodies.

2. Prior Art

Viral antibodies can be detected and quantitated by the so-called viral neutralization methods which may take up to 2 weeks to perform. A relatively recent method for determining Human Immunoglobulins is disclosed by S. E. Salmon et al. in an article entitled "Sandwich Solid Phase Radioimmunoassay for the Quantitative Determination of Human Immunoglobulins", in *J. Immunol.*, 103, 129–137 (1969). In U.S. Pat. No. 3,652,761 issued to H. H. Weetall on March 28, 1972, there is disclosed a method of isolating antibodies from a solution. The method involves reacting the solution with an immunochemical composite consisting of an appropriate antigenic substance coupled through an intermediate silane coupling agent to an iorganic carrier such as porous glass particles. By employing teachings in the above patent, it is possible to successfully couple antigenic substances such as viruses or virions to an inorganic support and use the resulting composite to extract corresponding specific antibodies from a solution. In preparing immobilized virus composites, it is desirable to achieve a fairly high loading of the virus on the carrier material. To a certain extent, such high loadings can be accomplished by using high surface area carriers such as porous glass particles. Unfortunately, however, many virus or virion preparations contain numerous other materials as impurities and those impurities may take part in the binding process, thus limiting the amount of virus that can be bound on the high surface area carrier. We have now found that by critically modifying the broad teachings of U.S. Pat. No. 3,652,761 and employing recent solid phase radioimmunoassay techniques, it is possible to load sufficient quantities of viruses or virions on porous glass particles such that it is possible to detect and quantitate viral antibodies in less than one day. Our method, and its use to detect and quantitate two types of equine anti-influenza virus antibodies is described in detail below.

SUMMARY OF THE INVENTION

Our method of detecting and/or quantitating anti-virus antibodies in a solution comprises the following steps:

A. reacting a solution of the serum containing an unknown amount of viral antibodies, a known amount of the antibodies which have been radioactively labelled, and a composite consisting of anti-virus antibodies coupled chemically through an intermediate silane coupling agent to a porous glass body, the composite having complexed thereto quantities of the virus with which the unknown antibodies and the labelled antibodies can complex;

B. separating the composite from the reaction solution;

C. determining the radioactivity count of either the separated composite or the remaining solution; and D. relating the count to a standard to quantitate, if any, the viral antibodies in the serum.

In a preferred embodiment, the porous glass body used as a carrier for the composite consists of porous glass particles described in detail below.

BRIEF DESCRIPTION OF THE FIGURE

The FIGURE illustrates the binding ability of three immunochemical composites at various serum dilutions for two different viral antibodies. The binding ability for each series of composites is represented in the FIGURE by plotting the percent of unbound antibodies against various dilutions of the sera containing specific antibodies.

SPECIFIC EMBODIMENTS

The immunochemical composites useful for our methods can be illustrated as:

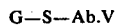

where G designates the porous glass body, S designates a silane coupling agent attached to the surface of G, Ab designates the viral antibody (identical to the antibodies to be detected and/or quantitated) coupled chemically to G through S, and V designates a virus or virion immunochemically complexed with Ab and capable of further complexation with labelled and unlabelled virus and virion specific antibodies in solution.

Porous glass bodies are well known (e.g., U.S. Pat. No. 3,790,475; U.S. Pat. No. 3,544,524; U.S. Pat. No. 3,485,687) and commercially available from several sources in various average pore sizes. In the examples below, we used porous glass in particulate form. We prefer to use porous glass particles having an average particle size between about 1 $\mu$ and 10 $\mu$ to assure reactant binding, minimize diffusion time and assure complexations within the pores, and sensitivity of the assay. Porous glass particles in that size range tend to remain in suspension in an aqueous medium. Our preferred average pore diameter range is between about 1000A and about 3000A, depending generally on such factors as the size of the antibody and virus or virion and the size and form of the porous glass body. Porous glass is an ideal carrier because of such properties as relative inertness, rigidity, and, very importantly, its high surface area. Preferably, the porous glass has a surface area of at least about 5 m²/g.

The porous glass body can be silanized by known methods and specific viral antibodies can be coupled chemically to the particles through the silane by a variety of methods (e.g., U.S. Pat. No. 3,652,761). Silane coupling agents are compounds having a dual functionality; a silicon portion which can be attached to many inorganic surfaces (e.g., glass) and an organo-functional portion which can be coupled to an organic compound (e.g., protein). Virus to which the coupled (or immobilized) antibody is specific can then be readily complexed with the composite to yield G—S—Ab.V. Our solid phase radioimmunoassay for viral antibodies can be schematically illustrated as follows:

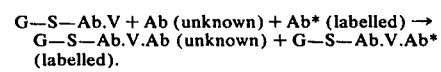

Ab (unknown) and Ab* (labelled) tend to compete in the incubation solution for a limited number of complexing sites on the G—S—Ab.V composite. Thus, by permitting the composite G—S—Ab. V to react with a solution containing Ab (unknown) and Ab* (labelled)

for a suitable reaction period sufficient to assure complexation at essentially all available sites on the bound Ab, and then separating the solution from the composite, it is possible to determine and/or quantitate the Ab (unknown) by counting the radioactivity of either the separated solution of the composite and relating the count to a standard such as a standard curve. A standard curve can be prepared beforehand by using known amounts of labelled and unlabelled antibodies. Labelled antibodies can be prepared by a variety of known methods (e.g., tritiation or iodination with $I^{125}$).

In our illustrative examples below, we show how to detect and quantitate two types of antibodies, each specific for different types of equine influenza viruses. The porous glass carrier (G) used to prepare the composite G—S—Ab.V consisted of porous glass particles having an average particle size between about 1 μ and 10 μ and an average pore diameter of about 1550A. Base porous glass, similar to that used is available commercially in 20–80 mesh particle sizes and such particles can be comminuted further to 1–10 μ average particle sizes in accordance with the general disclosure in patent application Ser. No. 447,250, filed in the names of F. Baker and D. Eaton on Mar. 1, 1974 entitled "Suspendable Porous Glass Particles", the patent application being assigned to the present assignee.

The porous glass carrier was silanized by known means using γ-aminopropyltriethoxysilane (A-1100, Union Carbide Corp.) and that silanized porous glass is referred to herein as alkylamine-glass.

The indicated viruses or "virions" and the indicated horse serum samples were obtained from Phillips-Roxane Laboratories of St. Joseph, Missouri. Our specific methods for preparing the G—S—Ab (immobilized antibodies) and G—S—Ab.V (immobilized antibodies having the specific viruses complexed thereto), as well as our assays for antibodies in the serum samples, were performed as indicated below. All incubation products were removed by centrifugation. Radioactivity counts were made with a gamma scintillation counter.

Assay for Antibodies in Serum

Two types of equine influenza virus known as the Prague (P) strain and the Miami (M) strain were used as described. The viruses were obtained in a freeze-dried state in fetal calf serum. The quantity of "virions" was $2.5 \times 10^7$/bottle. Antisera prepared in horses with the above viruses were found to be substantially "monospecific" for each virus type by viral neutralization tests in mice. The sera used in the examples and their neutralization titers were as follows:

| Serum | Titer |
|---|---|
| Horse No. 51 — Anti-Miami | Miami 1:4096<br>Prague <1:2 |
| Horse No. 30 — Anti-Prague | Prague 1:64<br>Miami <1:2 |

Preparation of Immobilized Antibodies (G—S—Ab)

Separate quantities of each type of sera were prepared as follows: Ten ml. of each horse serum was fractionated twice with 50% saturation in ammonium sulfate using the procedure described by E. Kabat, *Experimental Immunochemistry* 2nd Edition, Charles C. Thomas, Springfield, Ill., pp. 760–778 (1967). The final concentration of all globulin preparations was 30 mg/ml. To 0.23 g of the alkylamine glass particles was added 10 ml. of 2.5% glutaraldehyde. The aldehyde derivatives were washed thoroughly and then 1 ml. globulin fractions in 0.1M phosphate buffer, pH 7.0, were added to separate samples of the derivatized glass particles. The antibodies and derivatized glass particles were allowed to react for two hours at 0° C. and then washed and stored at 4° C. prior to use.

Preparation of the Viruses

The freeze-dried virus samples were brought to a final concentration of $5 \times 10^6$ virions per ml. by the addition of distilled water.

Preparation of Immobilized Antigen (G—S—Ab.V)

Separate preparations were made as follows: To 10 ml. of immobilized antibody (G—S—Ab) suspension at a concentration of about 10 mg/ml. was added 0.2 ml. of the final virus preparation. It is thought that this quantity can be varied somewhat for optimization of the product. The reactants were stirred for 2 hours to permit the virus to react (complex) with the immobilized antibodies. The pH was maintained at 7.2 with 0.025M phosphate buffer. The final product (G—S—Ab.V) was washed three times with the buffer solution before use.

Preparation of $I^{125}$ Labelled Antibodies (Ab*)

Samples of the above-described globulins were labelled with $I^{125}$ by the general method described by W. M. Hunter and F. C. Greenwood, *Nature*, Vol. 194, pp. 495–496 (1962) and stored frozen for later use in the assay.

EXAMPLES

In the following examples, varying dilutions of serum No. 30, serum No. 51, and a known double negative serum No. 27 (control serum O) were reacted with the indicated composites (G—S—Ab.V) of each virus stain (Miami-M and Prague-P). A total of six series (at varying serum dilutions) of reactions was run to determine the titer of each serum and show that the assay technique is successful. The reactions for each indicated series were initiated by adding to separate test tubes (in duplicate) the following amounts of reactants:

1. 0.5 ml. of the indicated serum at indicated dilutions of 1:2 to 1:64,000.
2. 0.1 ml. of the indicated immobilized antigen (1.0 mg) prepared with the indicated virus, e.g., G—S—Ab(M).V(M) and G—S—Ab(P).V(P), as indicated.
3. 0.1 ml. of the indicated labelled antibody globulins (Ab*), e.g., Ab(M)* and Ab(P)*, as indicated.

All reaction solutions were made up in 0.025M phosphate buffered solutions, pH 7.2, containing 0.3% bovine serum albumin (BSA). The experimental plan involved reacting the indicated dilutions of serum No. 51, serum No. 30, and control serum No. 27 with the immobilized composites of M and P viruses, e.g., G—S—Ab(M).V(M) and G—S—Ab(P).V(P), as indicated. Each reaction was in the presence of the indicated labelled antibodies, e.g., Ab(M)* or Ab(P)*. The six series of reactions can be summarized as follows:

Serum No. 51, Specific to M Virus, at Indicated Dilutions of 1:2 to 1:64,000 and Reacted as Follows -continued Series No. 1: Ab(M) + G-S-Ab(M) · V(M) + Ab(M)*
Series No. 2: Ab(M) + G-S-Ab(P) · V(P) + Ab(M)*
Series No. 3:     0 + G-S-Ab(M) · V(M) + Ab(M)*
Serum No. 30, Specific to P Virus, at Indicated
Dilutions of 1:2 to 1:64,000 and Reacted as Follows Series No. 4: Ab(P) + G-S-Ab(P) · V(P) + Ab(P)*
Series No. 5: Ab(P) + G-S-Ab(M) · V(M) + Ab(P)*
Series No. 6:     0 + G-S-Ab(P) · V(P) + Ab(P)*

* = $I^{125}$ labelled Ab
0 = double negative to V(P) and V(M) and diluted similar to serum No. 51

The reactants of each series were allowed to react overnight in a refrigerator although it is thought the reactions could also be carried out in a matter of a few hours at 23° C.–37° C. The solid phase reaction products in each series were then centrifuged out and washed once with the BSA buffer solution after the radioactivity of the final sediments were counted. In the FIGURE, the respective amounts (%) of labelled antibodies (Ab*) remaining in solution are plotted against the indicated serum dilutions, e.g., 1/dilution vs. 100%-% bound (or percent unbound).

The results of series No. 1 and series No. 4 are shown in the FIGURE where it can be seen that a useful slope developed at varying serum dilutions. The results of series No. 2, series No. 3, series No. 5 and series No. 6 were identical, e.g., non-specific. An example of this group of non-specific reactions is shown in the FIGURE as series No. 2. The results clearly show that our solid phase radioimmunoassay can be used to detect and/or quantitate the anti-viral antisera as indicated by neutralization titers. The data also indicated that by using the binding values at 20% binding, it is possible to obtain titers at least equivalent to the neutralization titers in less than one day while the neutralization method requires about 2 weeks. Although the above-described techniques show that the composite G—S—Ab.V can be successfully used to detect and/or quantitate two types of Ab specific to two types of respective V, it can be readily appreciated that, given this disclosure and the teachings of U.S. Pat. No. 3,652,761, a wide variety of different antibodies can be detected. The only requirement for preparing useful G—S—Ab.V composites useful for detecting any anti-viral Ab is that a sample of the Ab be capable of reacting with the organo-functional portion of the silane in such a manner that the Ab retains its ability to complex further with its specific V. U.S. Pat. No. 3,652,761 discloses various other techniques for modifying silanes (attached to any inorganic carrier) to yield biologically active (complexing) immobilized antibodies.

It should also be noted that virus detection and/or quantitation should be possible by modifying the above technique. For example, if unknown quantities of a given virus and a given amount of labelled antibodies (specific to the virus) are added, after a calculated delay, to a G—S—Ab composite, the quantity of labelled bound Ab should be a direct indication of the quantity of virus present. Such a reaction can be represented as follows:

G—S—Ab + V (unknown) + Ab* → G—S—Ab.V.Ab*

The amount of G—S—V.Ab*, which can be readily counted, is directly related to the amount of V present. Alternatively, the amount of Ab* remaining in solution after the reaction (incubation) period can be counted to determine the amount of Ab* complexed, and thus, the amount of V. Similarly, it is thought that other techniques will become apparent to those skilled in the art given the teachings herein.

Inasmuch as the above-described examples are merely illustrative of our disclosure, it is intended that the scope of the invention should be limited only by the appended claims.

We claim:
1. A method of detecting or quantitating anti-virus antibodies in a test solution which comprises the steps of:
  a. reacting the test solution containing an unknown amount of the viral antibodies, a known amount of the antibodies which have been radioactively labelled, and a composite consisting of the anti-virus antibodies coupled chemically through an intermediate silane coupling agent to a porous glass body, the composite antibodies having complexed thereto quantities of the virus with which the unknown antibodies and the labelled antibodies can complex;
  b. separating the composite from the reaction solution;
  c. determining the radioactivity count of either the separated composite or the remaining solution; and
  d. relating the count to a standard to detect or quantitate the viral antibodies in the serum.

2. The method of claim 1 wherein the porous glass body is in particulate form.

3. The method of claim 2 wherein the porous glass consists of porous glass particles having an average pore diameter between about 1000A and 3000 A and an average particle size between about 1 $\mu$ and 10 $\mu$.

4. The method of claim 1 wherein the composite of step (a) consists of a composite designated G—S—Ab.V where G represents the porous glass body, S represents a silane coupling agent attached to G at the silicone portion and coupled at the organo-functional portion to Ab, a viral antibody of the type to be detected or quantitated, and V represents a virus complexed to Ab and to which Ab is specific.

5. The method of claim 4 wherein the G—S portion of G—S—Ab.V represents the reaction product of a porous glass body and $\gamma$-aminopropyltriethoxysilane, the G—S—Ab portion represents the reaction product of that G—S, glutaraldehyde and Ab, and the G—S—Ab.V represents the reaction product of that G—S—Ab and V.

6. The method of claim 4 wherein V represents an equine influenza virus.

7. The method of claim 6 wherein the virus is of the Prague strain.

8. The method of claim 6 wherein the virus is of the Miami strain.

* * * * *